United States Patent [19]
Miyamoto

[11] Patent Number: 4,976,593
[45] Date of Patent: Dec. 11, 1990

[54] PULSATILE FLOW DELIVERY APPARATUS

[75] Inventor: Alfonso T. Miyamoto, Fukuoka, Japan

[73] Assignee: Meddiss, Incorporated, Fukuoka, Japan

[21] Appl. No.: 334,577

[22] Filed: Apr. 7, 1989

Related U.S. Application Data

[63] Continuation-in-part of Ser. No. 114,427, Oct. 29, 1987, abandoned.

[30] Foreign Application Priority Data

Dec. 3, 1986 [JP] Japan .................. 61-288363
Jan. 22, 1987 [JP] Japan .................. 62-7942[U]

[51] Int. Cl.$^5$ .................................. F04B 43/12
[52] U.S. Cl. ............................ 417/476; 417/479
[58] Field of Search .................. 417/474–478, 417/505, 479

[56] References Cited

U.S. PATENT DOCUMENTS

| 754,000 | 3/1904 | Munro | 417/476 |
|---|---|---|---|
| 3,431,864 | 3/1969 | Jones, Jr. | 417/475 |
| 3,437,050 | 4/1969 | Hrdina | 417/476 |
| 3,620,650 | 11/1971 | Shaw | 417/476 |
| 3,679,331 | 7/1972 | Kushner | 417/479 |
| 3,726,613 | 4/1973 | von Casimir | |
| 3,791,777 | 2/1974 | Papoff et al. | 417/475 |
| 3,811,800 | 5/1974 | Shill | 417/478 |
| 3,935,885 | 2/1976 | Alter | 417/476 |
| 4,012,176 | 3/1977 | Drori | |
| 4,165,954 | 8/1979 | Amos | 417/477 |
| 4,273,121 | 6/1981 | Jassawalla | 417/479 |
| 4,297,083 | 10/1981 | von Petery | 417/505 |
| 4,492,531 | 1/1985 | Kenji et al. | 417/477 |
| 4,568,255 | 2/1986 | Lavender et al. | |
| 4,651,490 | 4/1987 | Abbott | 417/505 X |
| 4,767,289 | 8/1988 | Parrott et al. | 417/477 |

FOREIGN PATENT DOCUMENTS

| 0071951 | 2/1983 | European Pat. Off. | |
| 0093542 | 11/1983 | European Pat. Off. | |
| 2052660 | 5/1971 | Fed. Rep. of Germany | |
| 1527784 | 4/1968 | France | |
| 2342078 | 2/1977 | France | |
| 12196 | 6/1848 | United Kingdom | 417/476 |
| 1330833 | 9/1973 | United Kingdom | 417/476 |

Primary Examiner—Leonard E. Smith
Assistant Examiner—Eugene L. Szczecina, Jr.
Attorney, Agent, or Firm—Nixon & Vanderhye

[57] ABSTRACT

A pulsatile flow delivery apparatus includes a horse shoe shaped raceway, a tube, a milking mechanism, an occlusive clamp and a control device. The tube is disposed along the raceway. The milking mechanism has a pivot shaft, a rotating arm fixedly secured to the shaft and one milking roller rotatably mounted on one end of the rotating arm. The occlusive clamp has a stationary component, a mobile component disposed in opposed relation to the stationary component, and an actuator connected to the mobile component for moving the mobile component toward and away from the stationary component to clamp and release the downstream portion of the tube. The timing of opening and closing of the occlusive clamp is controlled by the control device to produce a pulsatile flow.

9 Claims, 14 Drawing Sheets

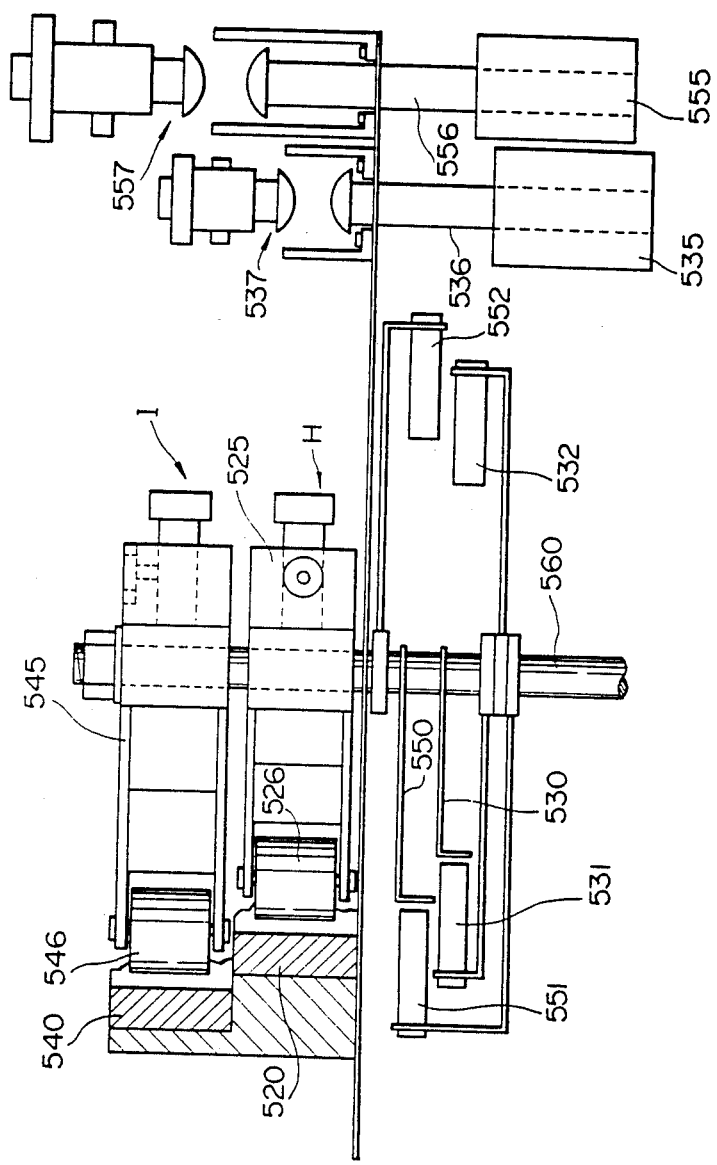

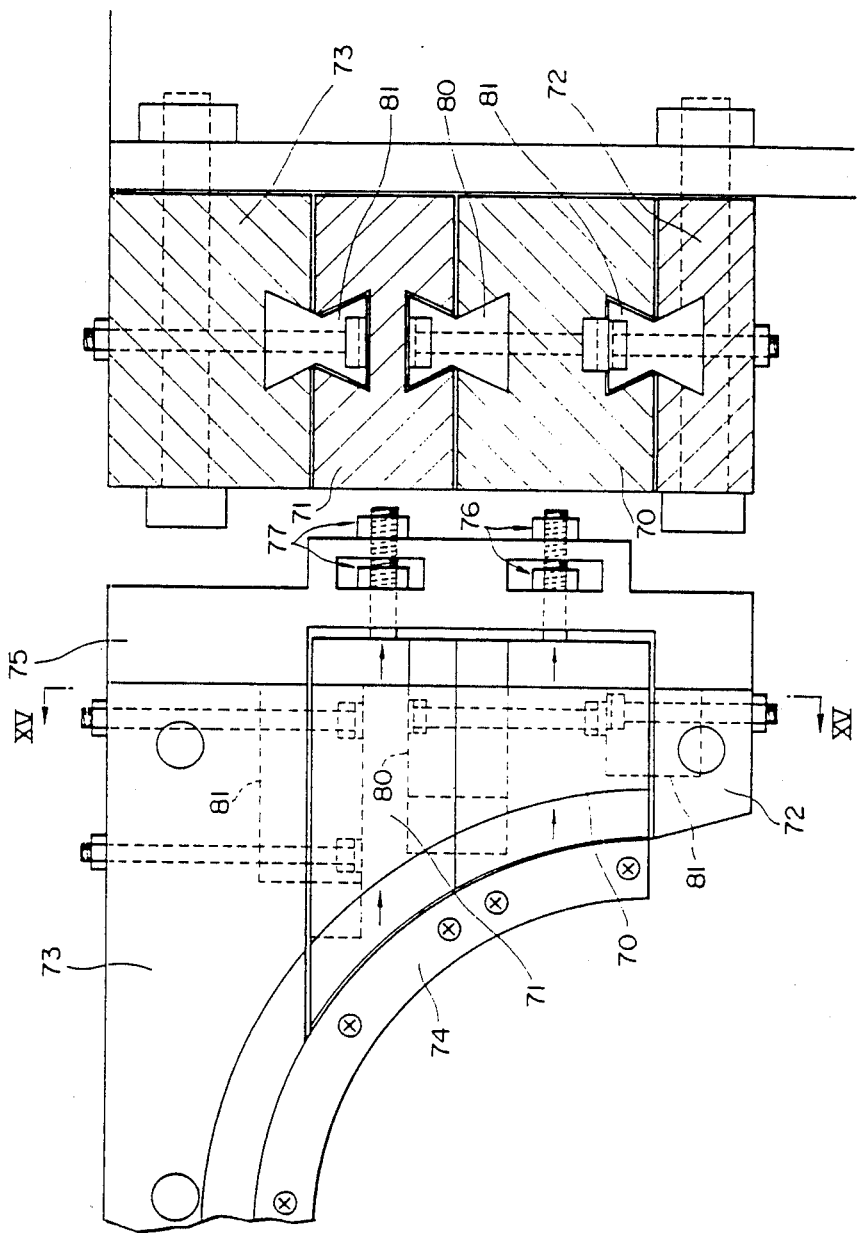

1

PULSATILE FLOW DELIVERY APPARATUS

CROSS-REFERENCE TO RELATED APPLICATION

This is a continuation-in-part of application Ser. No. 114,427, filed Oct. 29, 1987 now abandoned.

BACKGROUND OF THE INVENTION

1. Field of the Invention

This invention relates to a pulsatile flow delivery apparatus which can produce an arterial pulsatile pressure wave form close to that produced by the natural heart.

2. Prior Art

Conventionally, a pulsatile roller pump as shown in FIG. 1 has been used for extracorporeal circulation during either cardiopulmonary bypass or extended cardiac support or assistance. The pump is based on the principle of intermittently switching on and off the rotation of an arm 3 bearing two or three milking rollers 3a moving inside a horse shoe shaped raceway 1 that holds a tube 2, thus milking the blood (or any fluid) intermittently, i.e., in a pulsatile fashion. The speed of rotation is set so as to obtain the desired minute output at the set pulse frequency.

The currently available pulsatile pump, however, has three main shortcomings whose solution are desirable.

As shown in FIG. 2, the pulse wave of the pulsatile roller pump is the resultant of the summation of the sequential milking of each of the rotating two (or three) rollers, thus the pulse wave contour is scalloped or indented. Because of the inertia of the system, since the rotation of the roller bearing arm 3 has to go from zero to the maximum speed of rotation as preset by the required output in a short period, the velocity of pressure change or ascent slope of the pressure wave (dp/dt) is relatively slow with a relatively narrow pulse pressure and far from the natural cardiac beat pulse wave contour. Thirdly at high pulse frequency rates, the intended pulsatile flow becomes almost a constant flow type perfusion, i.e., the pump can not follow high frequency pulse rates.

SUMMARY OF THE INVENTION

This invention is therefore aimed at solving the above-mentioned shortcomings to provide a simple, economic and reliable pulsatile flow delivery apparatus which can produce an arterial pulsatile pressure wave form very close to that produced by the natural heart.

According to this invention, there is provided a pulsatile flow delivery apparatus, comprising: a horse shoe shaped raceway having an inner side of a prescribed curvature; a tube for flowing a fluid therethrough, the tube having a pump head portion disposed along the inner side of the raceway; milking means comprising a pivot shaft, a rotating arm fixedly secured to the shaft and a single milking roller rotatably mounted on one end of the rotating arm, the milking means being disposed so that, as the rotating arm rotates, the milking roller travels along the inner side of the raceway to squeeze the pump head portion of the tube against the raceway, to thereby milk the pump head portion intermittently as the rotating arm rotates; occlusive clamp means for opening and closing a portion of the tube downstream the pump head portion, the clamp means including a stationary component, a mobile component disposed in opposed relation to the stationary component, and an actuator connected to the mobile component for moving the mobile component toward and away from the stationary component to clamp and release the downstream portion of the tube; and control means connected to the actuator of the clamp means for controlling timing for opening and closing the clamp means to thereby cause the fluid to flow from the tube in a pulsatile fashion.

BRIEF DESCRIPTION OF THE DRAWINGS

FIG. 14 is a partial plan view showing a segmental raceway;

FIG. 15 is a cross-sectional view taken along the line XV—XV of FIG. 14; and

FIGS. 11, 13 and 17 are side-elevational views of the apparatuses of FIGS. 10, 12 and 16, respectively.

DESCRIPTION OF THE PREFERRED EMBODIMENTS OF THE INVENTION

Figure 1:
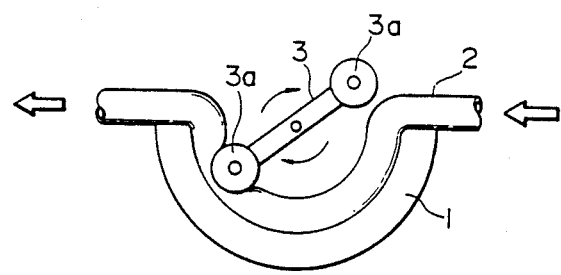
FIG. 1 is a schematic view showing a conventional two-roller pulsatile pump.
Figure 2:
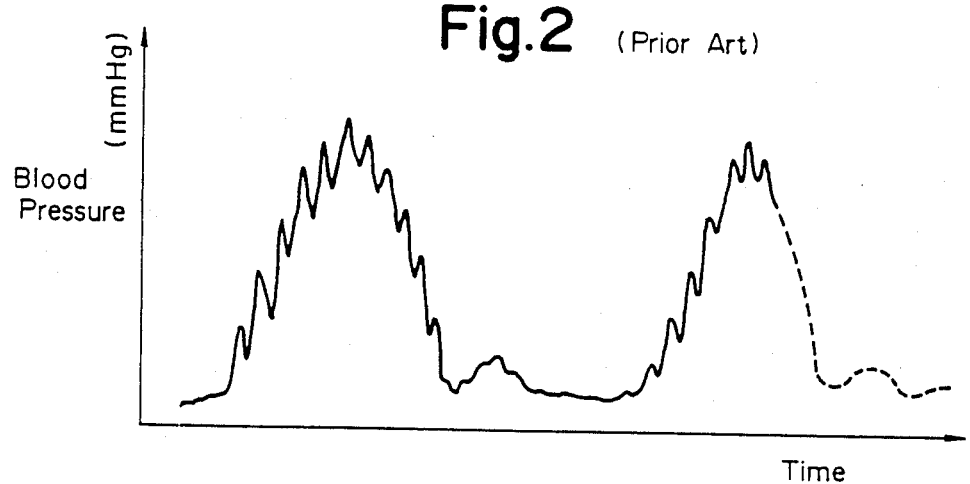
FIG. 2 is a diagrammatic view showing a wave pressure recording obtained with the conventional two-roller pulsatile pump.
Figure 3:
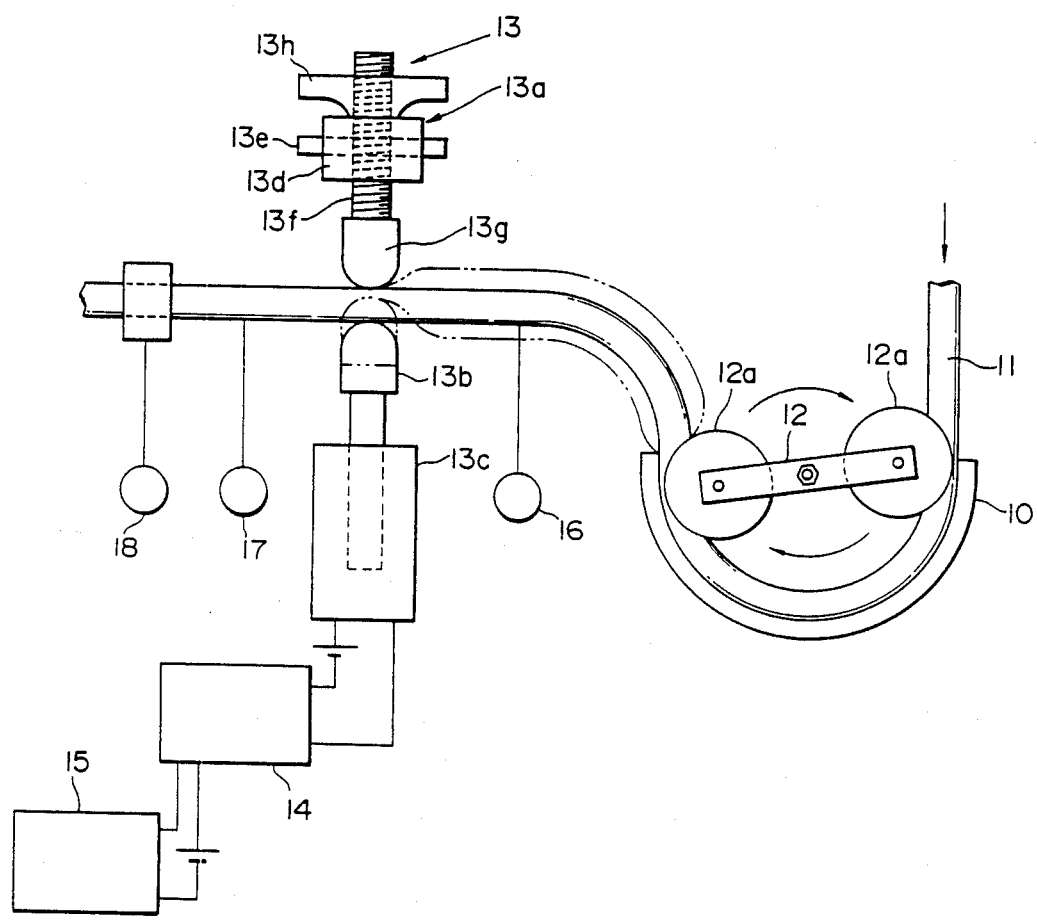
FIG. 3 is a schematic view showing a pulsatile flow delivery apparatus in accordance with this invention.

FIG. 3 depicts a pulsatile flow delivery apparatus in accordance with this invention being provided in conjunction with a conventional two-roller pump but could be a three-roller pump or a centrifugal pump instead. The apparatus includes a horse shoe shaped raceway 10 which holds, within its inner curvature, a pump head tubing 11, and a rotating arm 12 carrying two milking rollers 12a at opposite ends thereof. The pump head tubing 11 is made out of a material with a rubber hardness code of between JIS (Japanese Industrial Standard) 45° (SHORE(A) 45.92° (ASTM D-2240)) and JIS 55° (SHORE(A) 55.93°) which will allow storage of the stroke volume at an adequate intraluminal pressure when the outlet is intermittently occluded while the two rotating rollers 12a continuously propel blood (or any fluid) by their milking effect on the pump head tubing. The outlet of this tube 11 is held by a clamp 13 located at a specific distance from the end of the raceway 10. The clamp 13 has one stationary component 13a and one mobile component 13b that is moved up and down by a solenoid 13c. The stationary component 13a is comprised of a nut member 13e fixedly secured to a base (not shown) through a bracket 13d, a screw 13f threaded into the nut member 13e and having an occlusiveness control knob 13g at its one end, and a fixing nut 13h threaded on the screw 13f for fixing the screw 13f in the determined position by the nut member 13e. This clamp 13 occludes the outlet of the tubing 11 intermittently and at properly timed sequence, usually synchronized to the patient's electrocardiographic signal, or to the patient's pace maker or to an intrinsic device's signal picked up by an electrocardiograph 15, properly amplified and processed by a synchronizer 14 which in turn sends the final command signals to the solenoid 13c.

For proper monitoring of the perfusion, transducers 16 and 17 to measure intraluminal pressure of the tube compartment between the clamp and the pump, and downstream the clamp, respectively, as well as a flow measuring sensor 18 are used in this experimental prototype.

According to the structuration of this pulsatile flow conversion device the tube outlet clamp 13 actuated in a synchronized manner with the patient's electrocardiogram keeps the tube occluded during the patient's cardiac ejection, during which time the rollers 12a continue their milking effect and propelling of blood into the closed compartment of the compliant tube. As the stored volume of blood in this compartment increases, the intraluminal pressure continues to rise until the occluding clamp 13 opens, commanded by the synchronizing components 14 and 15, following the cardiac ejection, i.e., during diastole of the patient's cardiac cycle. The pressurized blood rushes downstream suddenly, i.e., in a pulsatile fashion into the patient's cardiovascular system. The rollers 12a maintain a constant flow at a rate determined by the set pump revolutions. The timing of the pulse and the duration of it can be freely adjusted and controlled by the component 14, and immediately from the pump rate.

Figure 4:
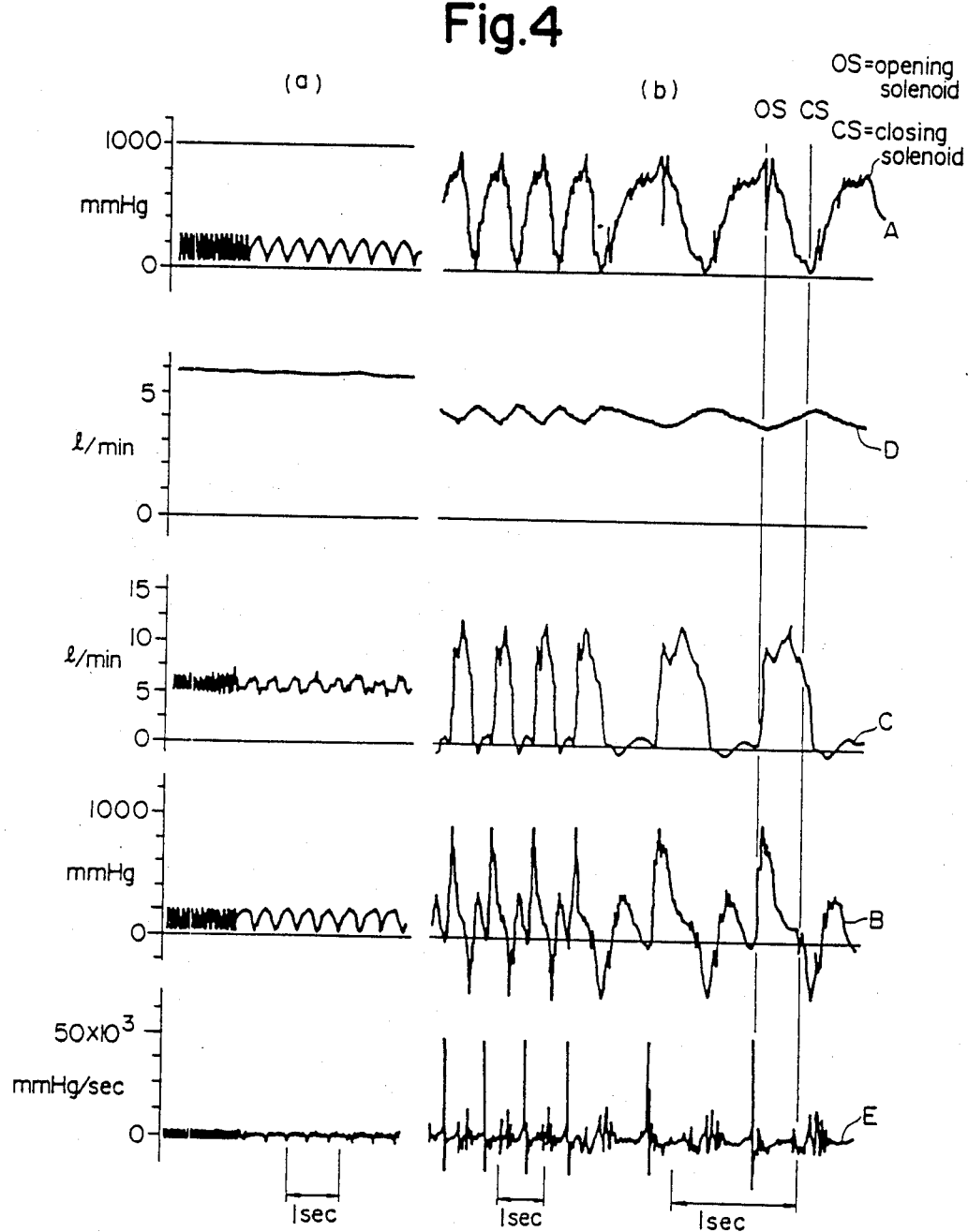
FIG. 4 is a diagrammatic view showing pressure and flow characteristics obtained with the apparatus of FIG. 3.

FIG. 4 is a recording obtained with the embodiment utilizing an intrinsic signal to drive the solenoid 13a of the clamp 13. The tracings of panel (a) on the left hand side are those obtained with the conventional two-roller pump operated in a non-pulsatile fashion; those on the panel (b) are tracings obtained with the same roller pump whose revolutions per minute are the same as in panel (a) but the pulsatile flow conversion device has been activated at a rate of 60 per minute. The tracing A was obtained via the pressure transducer 16 and illustrates the pressure change of the tube 11 compartment between the clamp 13 and the raceway 10; the tracing B was obtained via the pressure transducer 17 and illustrates the tube intraluminal pressure changes downstream the clamp 13; tracing C is the phasic flow recording, while D is the mean flow recording measured downstream the clamp 13. The tracing E is the dp/dt of pressure B and measures the rate of pressure changes in the tubing just downstream the clamp 13. The differences in the tracings of panel (a) and panel (b) are obvious and self evident; the indented or scalloped contour of the pressure tracing produced by the conventional roller pump contrast markedly with the clearly pulsatile pressure and flow tracing contour produced by the conversion of the same continuous flow using this pulsatile flow conversion device, which are quite close to those produced by the natural heart.

As described above, the pulsatile flow conversion device in accordance with this invention is provided in conjunction with standard conventional two or three roller pumps or centrifugal pumps. The apparatus requires the use of the perfusion tube 11 made out of a compliant material having a rubber hardness code of between JIS 45° (SHORE(A) 45.92°) and JIS 55° (SHORE(A) 55.93°) to allow compartmentalization of the apparatus and the creation of a pressurizing compartment between the outlet occluding clamp 13 and the pump head. The opening and closing of this clamp 13 mediated by the solenoid 13c is actuated by proper electronic synchronization to the patient's electrocardiogram, to a cardiac pacemaker or to an intrinsic pulse rate controlling mechanism.

Accordingly the continuous flow produced by the ordinary roller or centrifugal pump is intermittently stored for pressurization and released at a high pressure in a short time, thus converting the originally low pressure continuous flow into a more effective high pressure pulsatile flow. The created pulse wave contour is smooth and not scalloped, the pulse pressure is wider and with a higher dp/dt than those produced by the conventional pulsatile roller or pulsatile centrifugal pumps.

Since the tube outlet occluding clamp 13 is a separate entity from the pump itself and is driven by the solenoid 13c, it lends itself to easy synchronization with the patient's cardiac electrical activity, thus allowing the delivery of the pulsatile flow at the desired timing in relation to the cardiac cycle of the patient.

Figure 5:
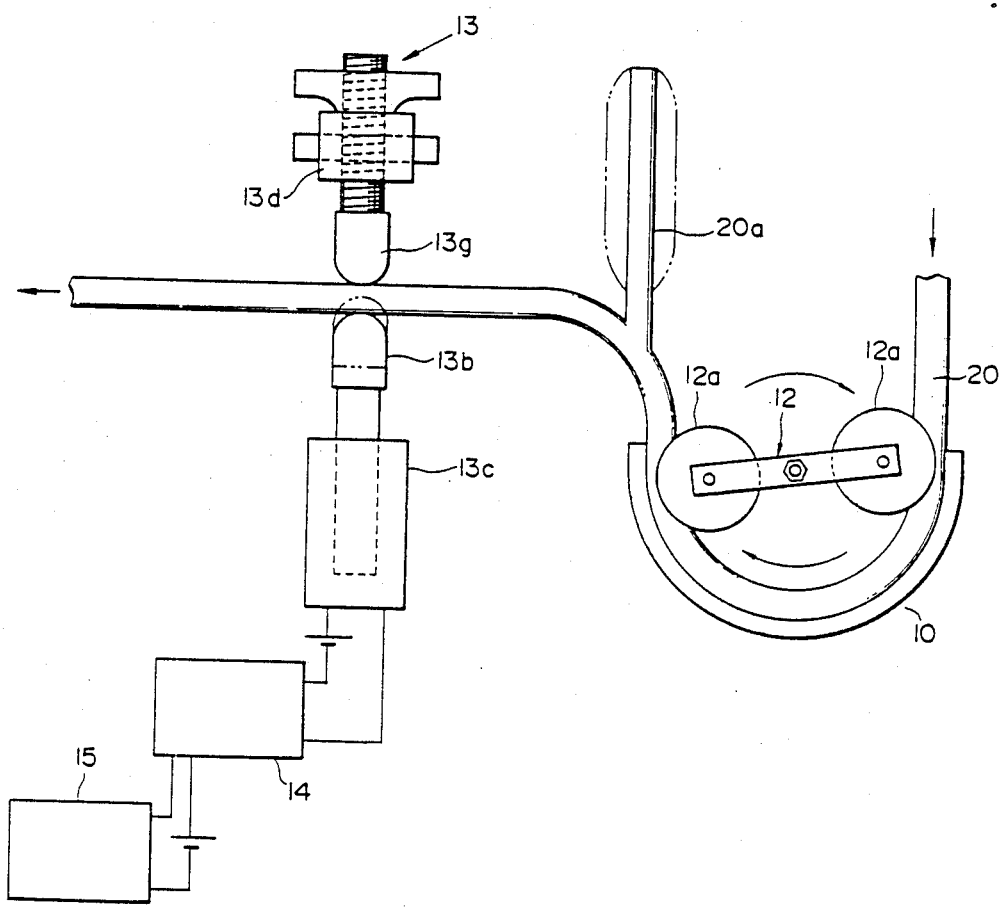
FIG. 5 is a schematic view showing a modified pulsatile flow delivery apparatus in accordance with this invention.

FIG. 5 depicts the application of this pulsatile flow conversion device with still a different arrangement of the compliant tube compartment. In this figure, the items in common with the previous arrangement are identified with the same numbers for simplification purposes. In this particular arrangement a commonly used somewhat rigid polyvinyl chloride tubing 20 has been used for the pump head. To create a pressurizing compartment downstream the pump (two or three roller pump or centrifugal pump) but upstream the occluding clamp 13, a compliant pouch 20a made out of a material with rubber hardness code of between JIS 45° (SHORE(A) 45.92°) and JIS 55° (SHORE(A) 55.93°) and with specific dimensions to produce the best pressure - volume curves for the specific needs has been connected just downstream the raceway 10 of the pump before the occluding clamp 13. Other than the fact that the pressurizing compliant compartment is now connected in parallel or "piggy bag" fashion to the main perfusion tubing, the function of the arrangement is identical to the previously described one in which the pump head tubing and a portion of the tubing itself, upstream the outlet occluding clamp 13, has been made using the compliant tube with rubber hardness code of between JIS 45° (SHORE(A) 45.92°) and JIS 55° (SHORE(A) 55.93°). The relative advantage of this new arrangement is economic, since it cuts down somewhat the length of the necessary compliant tube.

Figure 6:
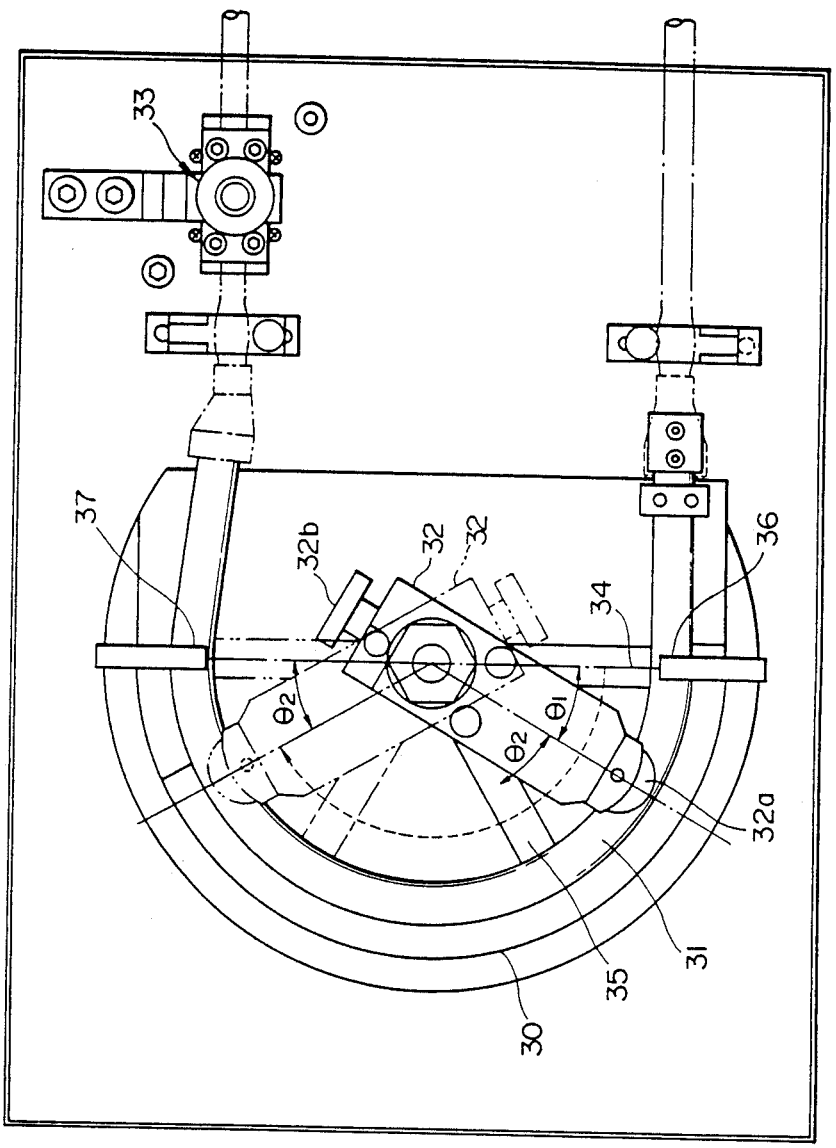
FIG. 6 is a plan view showing another modified pulsatile flow delivery apparatus in accordance with this invention.

FIG. 6 shows a further modified pulsatile flow delivery apparatus in accordance with this invention. The apparatus includes a horse shoe shaped raceway 30 with an arc of 180° to 190°, which holds a pump head tubing 31. The pump head tubing 31 is made out of a somewhat compliant material with a rubber hardness code of between JIS 45° (SHORE(A) 45.92°) and JIS 55° (SHORE(A) 55.93°), which avoids an excessive build up of the intraluminal pressure, and yet allows enough volume to be stored. A rotating arm 32, which holds a roller 32a at its one end and rotatable about a pivot shaft, is disposed adjacent to the raceway 30 for milking the tube 31. Similarly to the previous embodiments, the outlet of the tube 31 is placed within an occluding clamp mechanism 33 for occluding or opening the outlet of the tubing for the predetermined time.

The occlusiveness of the rotating roller 32a against the raceway 30 is controlled by an adjusting knob 32b which moves the roller closer to or away from the raceway 30.

The rotating arm 32 is provided with two reflecting plates 34 and 35 at two different height levels, both held by the same axis of the rotating arm 32. The reflecting plate 34 is phased $\theta_1$ angle counterclockwise to the rotating arm 32, and the reflecting plate 35 is phased $\theta_2$ angle clockwise to the rotating arm 32. Both plates can be fixed at various $\theta_1$, and $\theta_2$ angles. Two light sources and light sensors, 36 and 37, to sense the reflected light by the reflecting plates are mounted on the top of the raceway 30, each set at the proper height to meet the corresponding reflecting plate. The inlet sensor 36 is located at the beginning of the raceway 10; the outlet sensor 37 is mounted at the exit side of the raceway. The inlet sensor 36 is set to meet the reflecting plate 34, and the outlet sensor 37 is at the height to meet the reflecting plate 35. Proximity magnetic sensors could be used in lieu of the light sensors. When the sensor 36 senses the light beam reflected by the plate it sends a signal to the solenoid to open the clamping mechanism 33 of the outlet of the tube 31. When the sensor 37 senses its reflected light beam on the plate 35, it sends a signal to the solenoid to close the clamping mechanism 13 of the outlet of the tube. Thus the reflecting plates 34 and 35 as well as the sensors 36 and 37 make up the control mechanism of the clamp opening and closing the pump head tube outlet.

Accordingly, when the rotating roller 32a is off the raceway 30, the outlet of the pump head tube 31 is closed by the clamping mechanism 33. The rotating roller 32a starts its race on the raceway, and the milking effect on the pump head tube while the tube outlet is still closed. The intraluminal pressure of the tube increases as the rotating roller 32a races its way to the predetermined angle $\theta_1$, at which time the reflecting plate 34 is in front of the light source and sensor 36, thus the reflected beam is sensed by the sensor 36 which sends the signal to the solenoid to open the clamping mechanism 33 and the tube outlet is open. This results in a sudden flow of the pressurized contents of the tubing, in a pulsatile fashion, into the cardiovascular system of the patient. As the rotating arm 32 continues its rotation to the point where the reflecting plate 35 is in front of the sensor 37, the sensor 37 picks up the reflected beam and sends the signal to the solenoid to close the clamping mechanism 33 on the outlet of the tubing. The timing of this closure is set so that the tube outlet is clamped just before the roller 32a leaves behind the raceway 30, which assures a non regurgitant flow within the tube 31. The rotating roller 32a continues its rotation off the raceway to the next cycle, during which time the pressure within the pump head tube 31 should be theoretically zero or whatever pressure exists in the inlet tubing.

Figure 7:
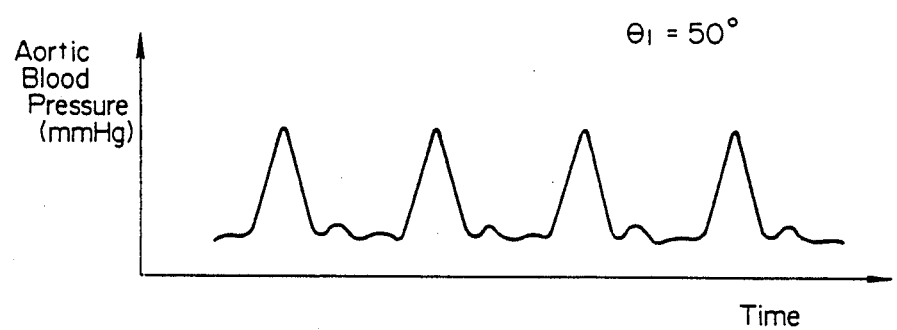
FIG. 7 is a diagrammatic view showing an aortic pressure recording obtained with the apparatus of FIG. 6, an angle $\theta_1$ being set at 50°.
Figure 8:
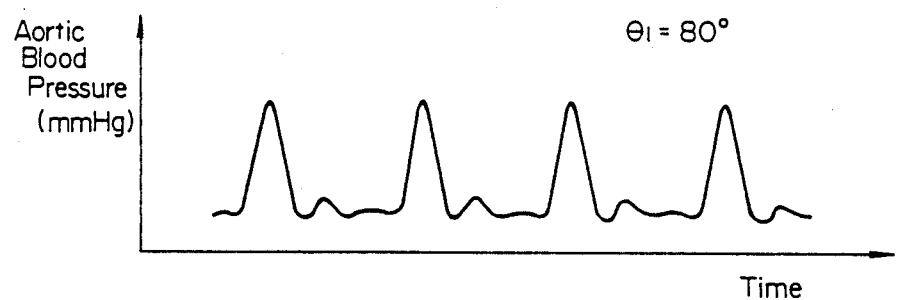
FIG. 8 is a view similar to FIG. 7, but showing the result with the $\theta_1$ set at 80°.

FIG. 7 illustrates the pressure wave contour of a pilot experiment in a goat. To be noted is the close resemblance to the pressure wave produced by the natural heart. Furthermore the pressure wave tracing of FIG. 7 was obtained at $\theta_1$ angle of 50°. By increasing the $\theta_1$ angle (pressurizing angle) to 80°, the rate of change of the upstroke slope, i.e., the dp/dt increases (FIG. 8).

These pressure characteristics are obtained because the physical properties of the pump head tubing maintains the intraluminal pressure changes within a relatively narrow range with volume changes. Thus the peak pressures of both FIGS. 7 and 8 experiments are close to 150 mmHg regardless of the $\theta_1$ angle, but the ascent slope is steeper in FIG. 8.

In the foregoing, when the pump is being used as a whole blood pump, there are limitations imposed by the tolerance of the formed elements of blood to compression and decompression, i.e., to sudden acceleration and deceleration. The tubing with the rubber hardness code of greater than JIS 45° is suitably used from this aspect. On the other hand, if the rubber hardness code of the tubing is less than JIS 45°, the peak pressure is too low, and the resulting dp/dt is low. Accordingly, the pulse wave characteristics obtained in the patients becomes less than optimal and therefore less effective.

An alternative to having two ($\theta_1$ and $\theta_2$ angle) adjustable reflecting plates as described, the sensors can be mounted on top of the raceway at the desired angle $\theta_1$ and $\theta_2$, thus requiring only one reflecting plate coaxial to the rotating arm 32. If the sensors are mounted on a holder that can be adjusted, the angles $\theta_1$ and $\theta_2$ can be varied even during rotation of the pump, i.e., without having to stop the pump.

Figure 9:
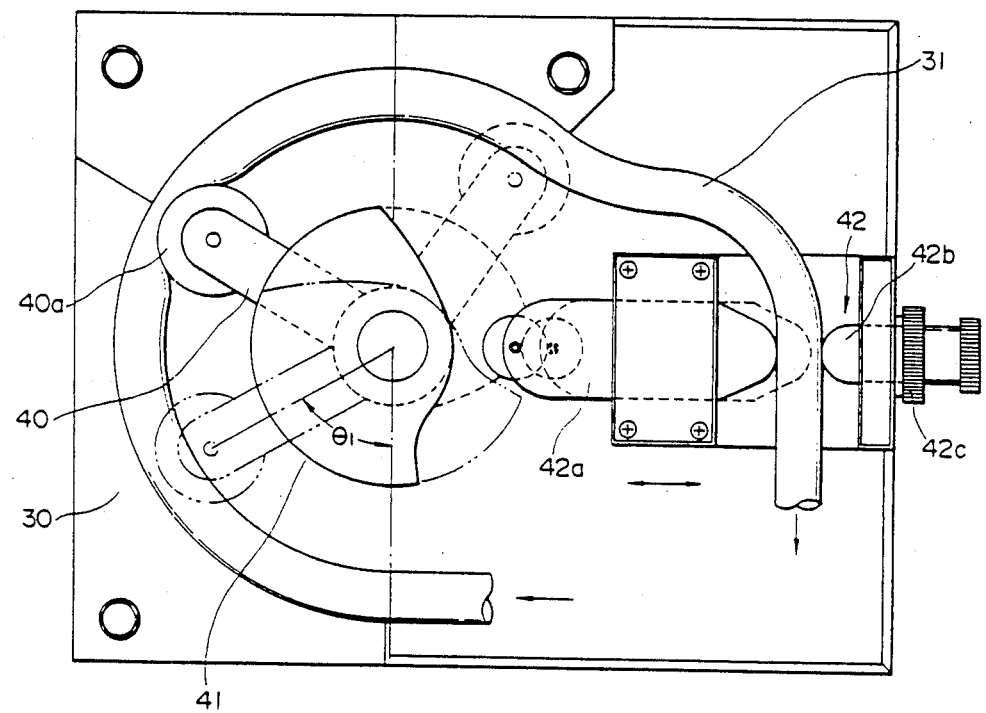
FIG. 9 is a plan view showing a further modified pulsatile flow delivery apparatus in accordance with this invention.

FIG. 9 depicts a further modified pulsatile flow delivery apparatus in accordance with this invention. The parts that are in common with FIG. 6 have been identified with the same numbers. A rotating arm 40 holding a rotating roller 40a is attached at its axis of rotation to a cam 41 or command controller of the opening and closing a tube outlet clamp 42. Opposing this cam 41, there is an occluding push rod 42a of the clamp that transmits and converts the circular motion of the cam 41 into a horizontal one. This occluding push rod 42a is kept in contact to the cam by a spring mechanism not illustrated in the figure. Opposing the free sided end of the occluding push rod 42a there is an occluder 42b of the clamp. The outlet of a pump head tube 31 is clamped between the occluding push rod 42a and the occluder 42b. Similarly to the previous embodiments, the occluder 42b has a mechanism 42c for adjusting the tubing occlusiveness. The shape of the cam 41 as well as the angle at which the cam 41 is to actuate the push rod 42a in relation to the location of the rotating arm 40 within the raceway 30 are designed to provide a pressurizing angle $\theta_1$. As illustrated by the broken line in the FIG. 9, the occluding push rod 42a keeps the clamp 42 closed for as long as the roller 40a is off the raceway 30 and for the pressurizing angle $\theta_1$ after the roller 40a has started its race on the raceway 30, at which point the cam 41 becomes operational, the occluding push rod 42a moves away from the occluder 42b and the clamp 42 opens. Just before the rotating roller 40a leaves the raceway, as illustrated by the two-dot chain line in FIG. 9, the cam 41 pushes back the push occluding rod 42a to the right of the Figure against the occluder 42b thus closing the clamp 42 controlling the outlet of the tubing 31. Thus the occluding push rod 42a and the occluder 42b make up the components of the clamp 42, whose command controller is the cam 41.

The pressure wave contour obtained by this cam driven clamp pulsatile pump is similar to that obtained by the solenoid clamp pump illustrated in FIG. 6. By designing a number of interchangeable cams with different $\theta_1$, and $\theta_2$ angles, or else an adjustable cam, the slope of the pressure change dp/dt as well as duration of the pulse can be modified to produce the best pressure wave contour for the patient.

An alternative to using a horizontal cam mounted on the same axis of the rotating roller arm to convert the circular motion into a horizontal motion is to use a corrugated belt to transmit the rotation of the main axis to a separate vertical cam, so that the push rod 42a moves up and down instead of horizontally, thus converting the rotational motion of the axis of the main pump axis into a vertical one.

As are the cases with the embodiments of FIGS. 3 and 5, the embodiments illustrated in FIGS. 6 and 9 are based on the interaction of two factors: the well known continuous flow pump function of the milking roller on one hand, and the compliance characteristics of the milked tube that enables storing pressure on the other. In the embodiments of FIGS. 6 and 9, however, to minimize unnecessary and potentially undesirable excessive build up of pressure during the time flow is interrupted to convert the continuous flow of standard two or three roller pumps into a pulsatile pump, only one rotating milking roller is provided. Since the horse shoe shaped raceway has an arc of 180° to 190°, a check valve mechanism must be incorporated in the form of a tube clamp on the outlet of the pump head tubing. By controlling the timing of opening and closure of this clamp in relation to the position of the milking roller on the raceway, the stored pressure in the tube before the clamp opens as well as the duration of the ejection in relation to the cycle of the pump can be adjusted to produce the best pulsatile characteristics of the pressure wave. The stroke volume, or volume ejected in each cycle, is determined by the capacity of the milked pump head tube sustained by the arc of the raceway that comes in contact with the rotating milking roller before the outlet clamp closes. Since each pulse is produced by one single revolution or cycle of the pump, the resulting pulsatile pressure wave contour is sharp and not scalloped as that produced by the existing two or three roller pumps. Since pressure can be stored before the actual flow starts, by controlling the opening time of the clamp, i.e., $\theta_1$ angle, adequate pulse pressures as well as a relatively steep ascent slope of the pressure wave dp/dt can be obtained and adjusted to each patient's condition to produce the pulsatile characteristics that resembles the patient's natural heart the most.

Further, in every day practice of cardiac surgery where the pulsatile flow delivery apparatuses are used, considerations other than the pump are important to keep in mind. The pump is only one half of the total cardiopulmonary bypass set, the other half is the artificial lung or oxygenator. Current commercially available oxygenators were all designed to be used in conjunction with continuous flow pumps, roller or centrifugal, placed upstream or downstream to the pump, and for flows of up to 6 liters/min only. The required oxygenator outlet connector to fulfill this relatively low flow rate is 9 mm in lumen, which is inadequate when pulsatile pump systems are used even at flow rate of less than 6 liters per minute.

For pulsatile perfusion with the monoroller pump using any of the available oxygenators and flows in excess of 5 liters/min, changes will have to be made in the design and capabilities of the oxygenators (unlikely to occur ever), or some ingenuity exercised in order to overcome these physical constraints imposed by the design of the oxygenators. A separate conventional two roller pump assigned to guarantee the filling of a specially designed inlet reservoir having larger diameter tubing, in order to meet the high flow requirements of the monoroller pulsatile pump, is the only solution until such time comes when manufacturers of oxygenators make the proper changes to meet the high flow requirements of this type of pulsatile pump. Meanwhile, the need for controlling two pumps simultaneously is somewhat cumbersome, and its solution is desirable to safely conduct the perfusion of the patient.

In view of the foregoing, the inventor has developed a dual roller pump which combines actually two pumps in one: the monoroller pulsatile pump, and the conventional two or three roller pump. Both pumps share the same power source or motor and the same axis of rotation, i.e., they are superimposed. Therefore both pumps have the same speed of rotation. To provide similar flow rates at any given revolutions per minute, the raceways for the two pumps are of different diameters, and arcs. The raceway for the monoroller pump must be larger than the raceway for the two-roller pump. Additional compensation of flow is achieved by using different tubing diameters for the pump head portion. At any rotation speed the flow of the conventional type two-roller pump must exceed that of the monoroller pulsatile pump, which necessarily keeps the inlet reservoir of the monoroller pulsatile pump totally filled at any time; the excess flow is overflowed back to the oxygenator or the venous reservoir. To control the flow rate of this dual pump, only one control knob needs to be manipulated. Once the system is set, its operation is as easy as operating the singular monoroller pulsatile pump or the conventional two-roller pump.

If the outlet clamp of the monoroller pump is made to be driven by a solenoid instead of a cam, the conventional two-roller pump can be converted into a pulsatile flow conversion device by borrowing the clamp of the monoroller pump. The solenoid of such clamp should respond to the two separate command signals, i.e., the signal from the monoroller pump or the signal synchronized to the electrocardiogram, cardiac pacemaker or an intrinsic trigger mechanism as described previously to function as a pulsatile flow conversion device independently but not simultaneously. The selection is to be made with an external switch type selector. Thus, this dual roller pump can be used as such or singularly as a pulsatile monoroller pump, as a pulsatile flow conversion device or as a conventional two-roller pump.

Figure 10:
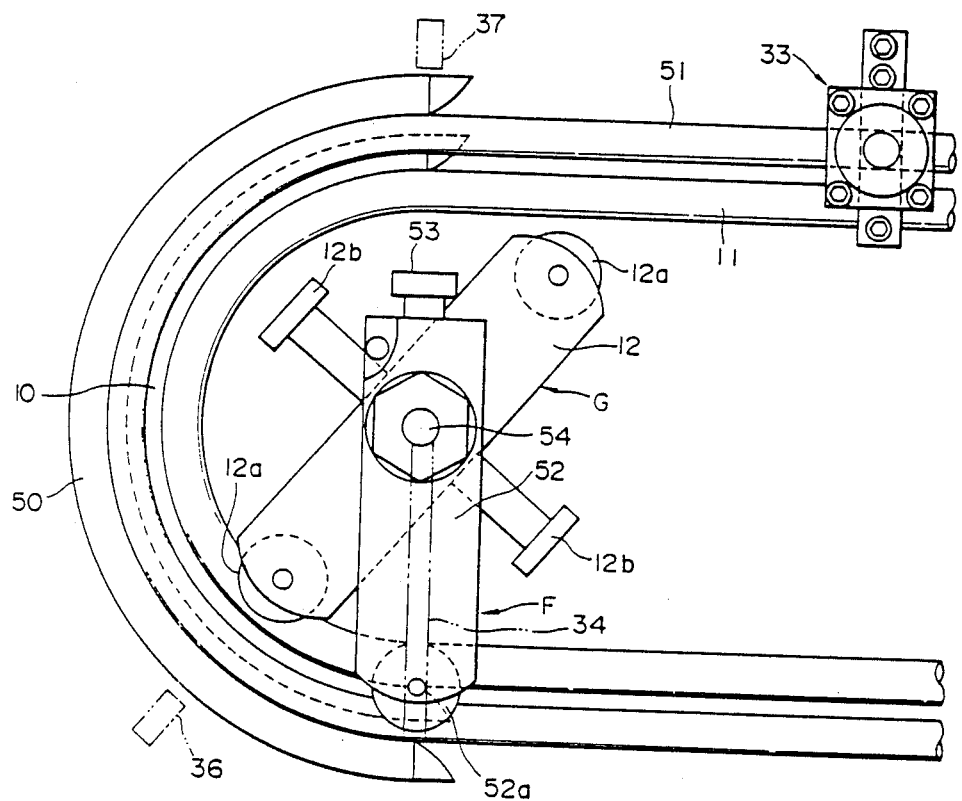
FIGS. 10, 12 and 16 are plan views showing further modified pulsatile flow delivery apparatuses, respectively.
Figure 11:
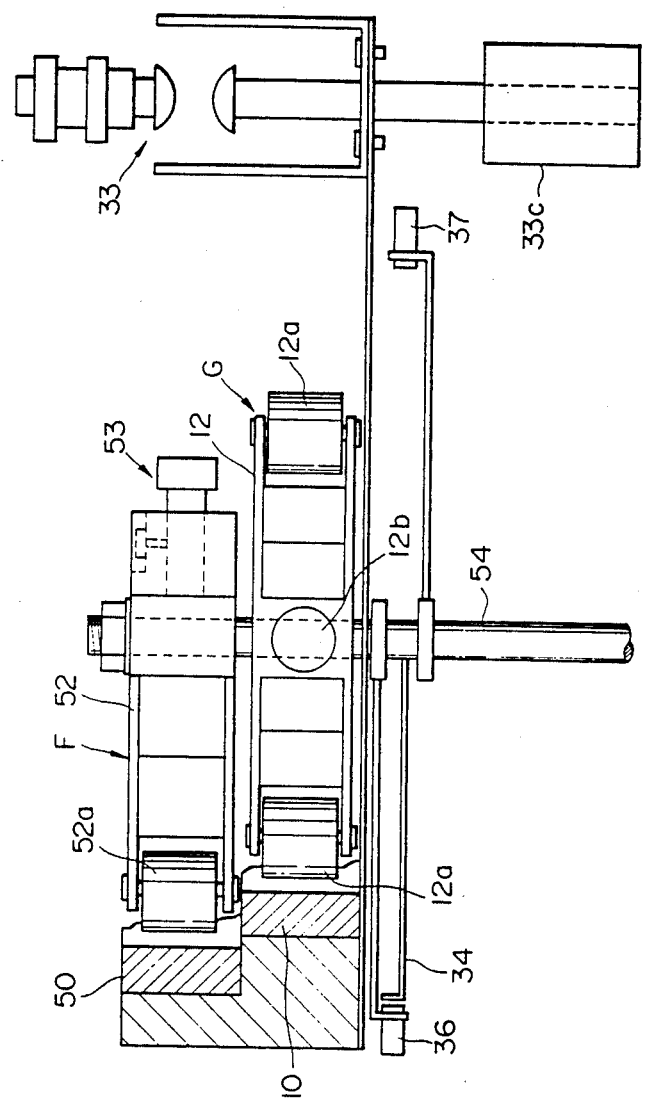

FIGS. 10 and 11 illustrate one such dual pump which is comprised of a pulsatile monoroller pump F and a two-roller pump G.

The horse shoe shaped raceway 50 with an arc of 180°–190° assigned to the pulsatile monoroller pump F is larger in diameter than the raceway 10 for the two-roller pump G, and occupies the upper deck. The respective roller bearing rotating arms 52 and 12 have different lengths, commensurate to the diameter of the raceways and hold one or two rollers 52a, 12a. Both rotating arms 52 and 12 are fixed to the same rotational axis 54. The rotating arms 52 and 12 have built in their respective roller occlusiveness control mechanisms 53 and 12b. The tube outlet clamp 33 is identical to that described in the aforementioned embodiments and will be simplified, except that its solenoid 33c has been made to respond separately to two commands originated either by the sensors of the monoroller pump F when used as the clamping mechanism for the pulsatile monoroller pump, or the patient's electrocardiogram, cardiac pacemaker or an intrinsic rate controller, when used as the clamp mechanism for the pulsatile flow conversion device.

A light reflecting plate 34 has been attached to the main rotational axis, parallel to the rotating arm 52 of the monoroller pump F, but within the pump casing, i.e., within the box containing the motor. Inlet and outlet sensors 36 and 37 are located also within the pump casing and fixed in such a manner as to allow adjustment of the $\theta_1$ angle (pressurizing angle) with the inlet sensor, and the timing of outlet clamp closure with the outlet sensor from the outside of the box, and while the pump is in operation. Accordingly if two tubes 51 and 11 are placed in their respective raceways 50 and 10, the activation of the dual pump will produce pulsatile flow in one and continuous flow in the other. The two-roller pump flow is greater than that produced by the monoroller pulsatile flow. If a specially designed reservoir with proper size inlet and outlet tubing is placed in series, downstream the two roller pump G but upstream the monoroller pump F, instantaneous stroke flow rates that are adequate for the monoroller pump inlet can be assured at all times. Since the two-roller pump flow rate is greater than that of the monoroller pulsatile pump, it will assure complete filling of the reservoir. To avoid over filling and bursting of the reservoir, the excess flow should be overflowed back to the oxygenator or the venous reservoir upstream the oxygenator.

This dual pulsatile pump allows pulsatile perfusion in conjunction even with hollow fiber type oxygenators that have a high pressure gradient This type of oxygenators were designed to be placed downstream a two-roller or centrifugal type pump. Because of their excessive resistance they are not suitable to be used with the pulsatile monoroller pump. By placing these type of oxygenator downstream the two-roller pump G of this dual pump, but upstream the inlet reservoir of the monoroller pump F, pulsatile perfusion is just as easy as if a bubble type oxygenator upstream the two-roller pump had been used. Since there is only one control to manipulate both pumps, its operation is as simple as that of any standard roller pump.

Obviously if only one tube is placed in either of the raceways, the dual pump can be used singularly under the designated mode of function, either as the standard conventional two-roller pump or the pulsatile monoroller pump. However, the solenoid driven tube outlet clamp can be used as pulsatile flow conversion device when combined to the two-roller pump. The solenoid should be activated by a command system other than that of the monoroller pump sensors. The patient's electrocardiogram, a cardiac pacemaker or an intrinsic system can be chosen to activate the solenoid. Used as a pulsatile flow conversion device will have certain advantages in terms of synchronization with the patient's cardiac activity.

Thus, the dual pulsatile pump has the versatility of all three perfusion modes: continuous flow, ECG synchronized pulsatile flow, and non-synchronized pulsatile flow perfusion. By proper setting of the extracorporeal perfusion circuit, these modes of perfusion can be changed freely without the need of stopping the pump at any time, since it only requires opening or closing a bypass line.

An alternative to combining the solenoid type monoroller pump with the standard two roller pump to make the dual pulsatile pump, is to use the cam type monoroller pump instead. This version of the dual pulsatile pump, however, can not be used as a pulsatile flow conversion device since it lacks from the solenoid mechanism to drive the outlet clamp.

Further, pulsatile perfusion is considered to be most physiologic mode for extended cardiac support or ventricular assist devices. The simplicity of the monoroller pulsatile pump and the economic implications of such system for not requiring expensive cardiac valve prosthesis make this monoroller pulsatile pump a very attractive pump for such purposes, i.e., as a ventricular assist device. Patients requiring mechanical ventricular assist of this type, often need the support of both sides of the heart, i.e., the left and the right ventricles.

Two independent pumps can be used for separate support of each side of the heart. However by applying the same principle outlined in the dual roller pump, two monoroller pulsatile pumps can be superimposed to solve the problems of having to operate two pumps with two controls.

Since the right and left heart usually have a different output and need a different flow rate assistance when cardiac support is needed, ways to provide different flows at the same speed of rotation must be incorporated in such pumps.

In view of the foregoing, the inventor has developed a biventricular assist dual monoroller pump which comprises two monoroller pulsatile pumps.

The two superimposed monoroller pulsatile pumps share the same axis of rotation, but have different diameter raceways, although with the same arc angle. The clamp mechanism must be independently assigned to each roller so that the opening and closure time of the tube outlet could be separately adjusted. The stroke volume, which is a function of the effectively used length of the raceway before the clamp closes the tube outlet, could be changed to a considerable extent, so that the total flow of one of the pumps could be changed independently from the other while maintaining the same pulse rate or r.p.m.. The pulsatile monoroller pump to be assigned to assist the right side of the heart is the one with the smaller diameter raceway, and should occupy the lower deck of the two superimposed roller pumps. For a given diameter raceway and pump head tubing size, the stroke volume can be decreased by closing the outlet clamp earlier than in the normally used position of full arc raceway. However, closing the clamp earlier will produce variable degrees of pressurization within the pump head tube. It is desirable to avoid unnecessary excessive pressurization of the tubing contents when the clamp is made to close considerably earlier than the initially needed full arc of the raceway for full flow assistance. An adjustable modular arc segmental raceway, designed so that a specific arc segment or segments of the tail end of the raceway could be slid out sequentially away from the roller path, will adjust the effective raceway arc to the newly set earlier clamp closure time. This design should allow adjustment of the arc or length of the raceway without the need of stopping the pump. Thus the stroke volume of the lower deck pump could be drastically decreased without altering the upper deck pump stroke volume, nor r.p.m. or minute volume. The end result is a considerably different minute volume for each of the pumps.

An alternative to having an adjustable modular arc segmental raceway to control the stroke volume, is to delay the closure of the outlet clamp beyond the length of the raceway. This will create a transient regurgitant or back flow before the next ejection. By controlling the duration of this back flow, the net forward minute flow could be controlled. This arrangement has the advantage of maintaining the largest stroke output possible for the tubing size used, thus minimizing the possibilities of blood clotting inside the tubing, since a relatively high r.p.m. (or pulse frequency) could be maintained even at low flow rates. A desirable by-product of this arrangement is the wide pulse pressure in the patient's cardiovascular system with its inherent physiologic advantages even during low flow rate perfusion, a feature not available in any of the currently used, specifically designed pumps for assist purposes, i.e., the pneumatically or electrically driven, valved, sac or pusher plate type pump.

Combining both methods, i.e., the adjustable modular arc segmental raceway and the delayed closure of the outlet clamp will increase further the capabilities to control the forward output, since the stroke volume decreases by the virtue of shortening the effective length of the raceway and the regurgitant time period increases, so the net forward flow decreases further.

Figure 12:
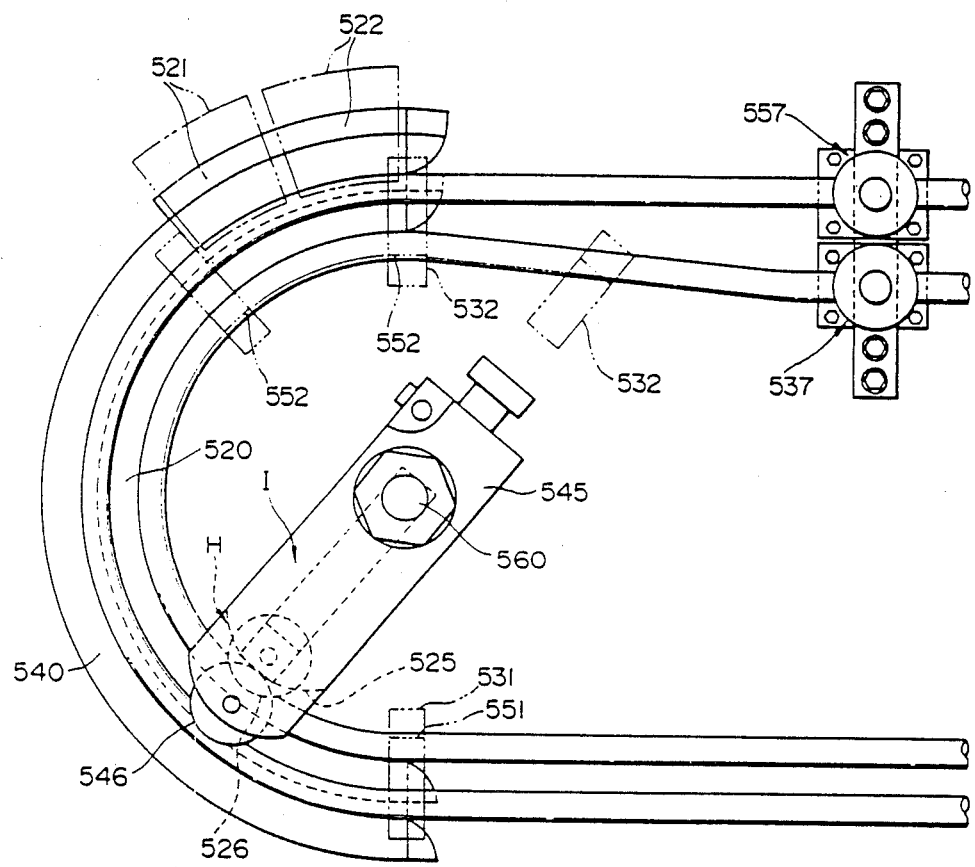

FIGS. 12 and 13 depict a biventricular assist dual pulsatile monoroller pump which comprises lower and upper solenoid type monoroller pulsatile pumps H and I. The lower deck pump H is assigned to be used for support of the right heart, and the upper deck pump I for the left heart. The lower deck pump H has a smaller diameter raceway 520. The tail end of this raceway 520 is modular and has two segments 521 and 522 of the raceway arc that can be sequentially slid out away from the roller pathway. Light sensors and light reflecting plates have been attached underneath the top of, and within the pump case. There is only one reflecting plate 530, 550 for each of the pumps which is fixed to a rotating axis 560 of the pump exactly underneath and parallel to rotating arms 525 and 545, the reflecting plate 530 being for the pump H while the reflecting plate 550 is for the pump I. The opening sensors or pressurizing angle sensors 531, 551 are independently adjustable between 0° and 90°; the closing sensors 532, 552 are adjustable between 90° and 330° to be used normally at 180°. The sensors 531 and 532 are for the pump H while the sensors 551 and 552 are for the pump I. These sensors should be adjustable from the outside of the pump case and while the pump is in operation. These sensors send their respective signals to their respective solenoids 535, 555, the solenoid 535 being for the pump H while the sensor 555 is for the pump I. Two identical sets of clamps, 537 for the pump H and 557 for the pump I, are required, each with their independent tube occlusiveness control 538, 558 as well as their respective occluding push rods 536, 556 to transmit the motion of the solenoids. The roller bearing rotating arms 525 and 545 have built in their respective roller occlusiveness control mechanisms 527 and 547, so that each roller occlusiveness can be adjusted separately.

In the wedge type arc segments design depicted in FIG. 12, a segment of the arc subtended by two radii of the raceway has been made to slide in and out the roller path. However it is technically simpler to build it with rectangular blocks instead of wedges, as shown in FIGS. 14 and 15. These blocks 70 and 71 can be fastened to each other by wedge type locks 80 and 81, which allow longitudinal displacement but no other motion of the blocks or segments.

The tail end or exit side of the raceway has been divided in 4 segments 70, 71, 72 and 73, each having basically a rectangular shape. Of these, segments 72 and 73 are stationary. The segment 73 is the main body of the raceway. The segment 72 is actually not a part of the raceway in itself, but is an extra segment that has been added to provide an anchoring point for the sliding components. The segments 70 and 71 are the two sliding raceway arc segments, and are held between the stationary segments 72 and 73. In order to provide the ability to slide in and out the roller path, these sliding segments are fastened to each other and to the stationary components with either wedge shape or rectangular shape rail type interlocking fasteners 80 and 81. In this embodiment, the two fasteners 81 adjacent to the stationary components are attached to their respective stationary segments. The fastener 80 is attached to the sliding segment 70. Thus the segments 70 and 71 can be slid out sequentially in that order. The interlocking fasteners 80 and 81 will provide the stability in terms of up and down motion of the sliding segments. In order to maintain the uniform occlusiveness of these raceway arc segments when being used as raceways, those sliding segments must be firmly secured against an inner stopper 74 with a convexity that conforms exactly to the concavity of the raceway arc segments. In the illustrated Figure, the components 75, 76 and 77 constitute the elements that move and fix the sliding segments. The component 75 is stationary and holds the mast bolt attached to the sliding segments. By a double nut system 76, 77 screwed on this mast bolt the sliding segments 70 and 71 can be not only slid in against the stopper 74 or out away from the stopper, but also they can be fixed and locked in the desired position.

The capabilities of adjusting forward flow while maintaining the same r.p.m. of the pump by the means of these adjustable raceway arc segments lend itself to its utilization to make fine flow rate self adjustment (servo control). A mechanism to slide these arc segments electronically in response to a specific change occurring in the patient or within the tubing system, such as left or right atrial pressure, or pressure within the tubing upstream the pump head should accomplish such servo control automation. To prevent back flow, this electronic control should adjust the tube outlet clamp closing timing as well, to change the closure of the tube outlet to make it adequate for whatever length of the raceway arc. However, since the raceway is shortened only when the forward flow needs to be decreased, some degree of back flow may be in fact desirable as an additional means to curtail forward flow of the pump, and for this, manual adjustment of the clamp closure time may be more advantageous.

Figure 16:
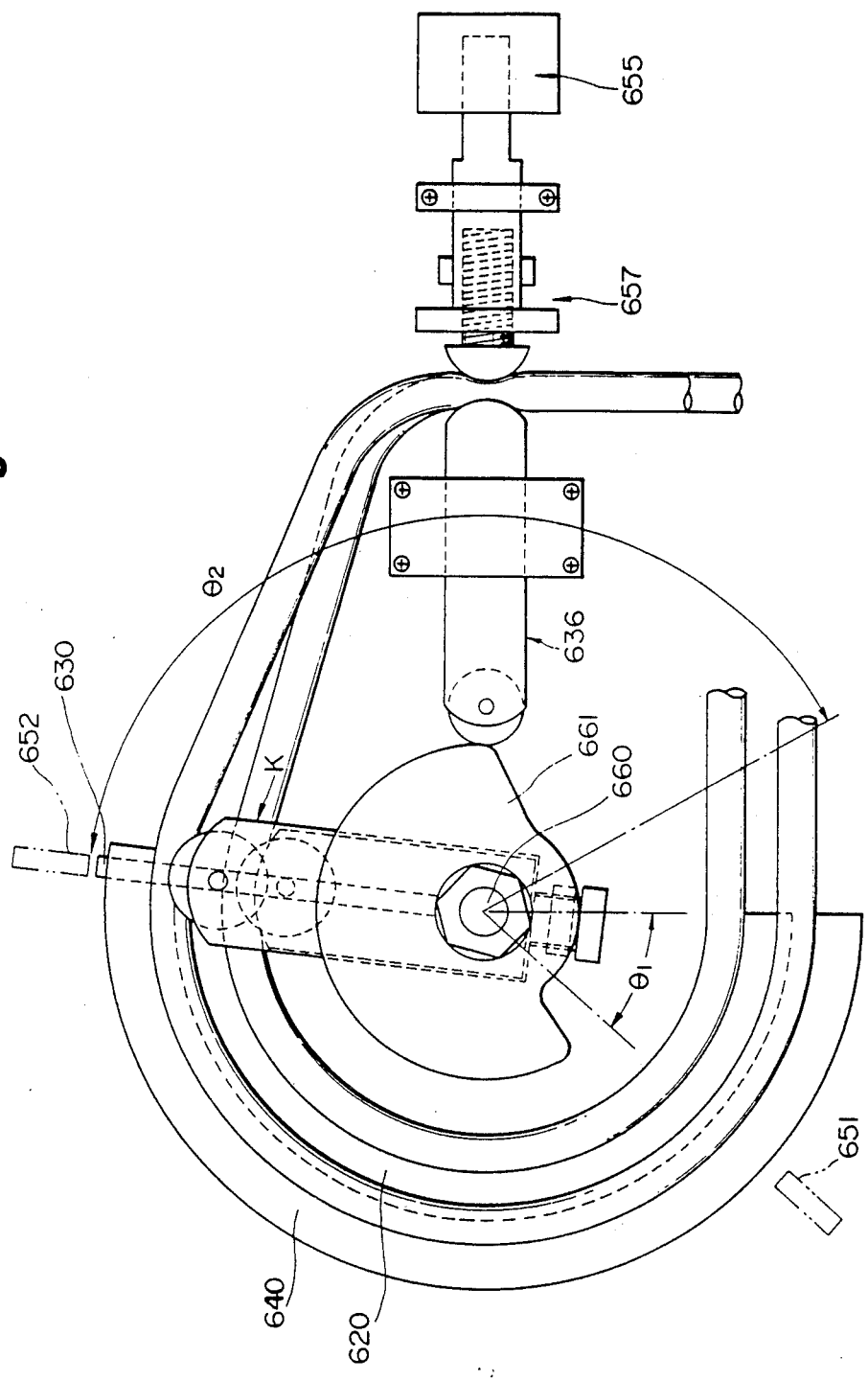
Figure 17:
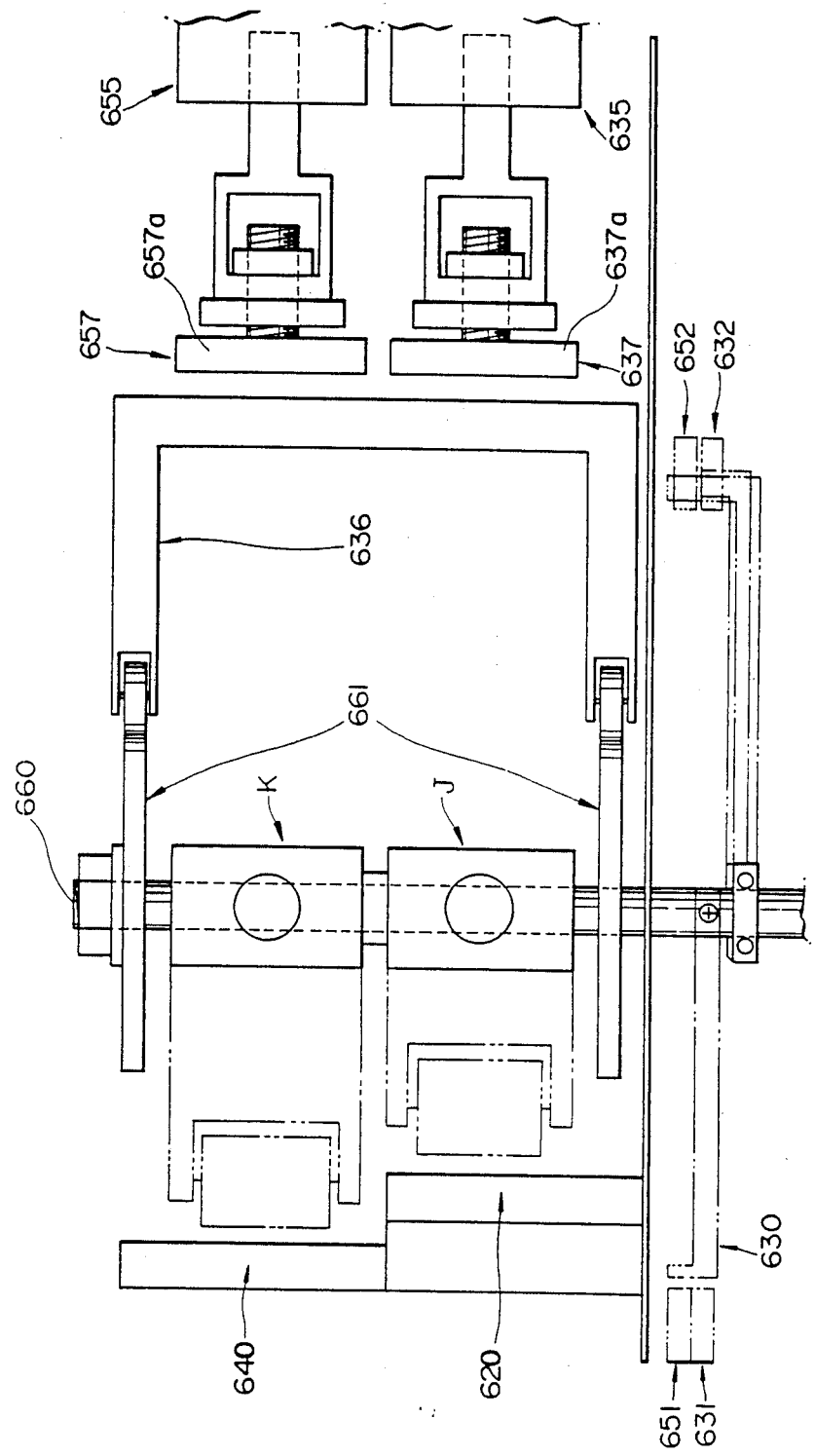

FIGS. 16 and 17 depict the biventricular assist dual pulsatile monoroller pump made out of two superimposed cam type monoroller pulsatile pumps J and K. The cam type monoroller pulsatile pump is less versatile than the solenoid type to alter the stroke volume without changing pump head tubing or stopping the pump, since the outlet clamp is actuated mechanically. However, by modifying the stationary component of this clamp it can be made to close with variable and controllable delay to induce the transient back flow.

The two superimposed monoroller pumps J and K share the same rotational axis 660; the lower deck pump J has a smaller raceway 620 than the upper deck pump K. The cam 661 is comprised of upper and lower members and common for both outlet clamps 637 and 657 which share the same moving occluding push rod 636. However the opposing stationary occluders 637a and 657a are separate. This stationary occluder has been modified to make it actually mobile independently from the cam, mediated by a solenoid 635, 655. When deactivated the solenoid 635, 655 moves the stationary occluder 637a, 657a of the clamp 637, 657 away from the push rod 636, thus maintaining the clamp actually open, until the solenoid 635, 655 is activated again. A reflecting plate 630, common for the sensors of both pumps, is attached to the main rotational axis inside the box of the pump, underneath the top table of the pump, and exactly parallel to the rotating arms of the pumps. The sensors that send the signals for activation of the solenoids to close or open their respective clamps are separate; the timing for closure of each of the clamps is independently controllable from the outside of the pump box, thus the duration or amount of the transient back flow can be varied from zero to whatever angle has been chosen in order to adjust the net forward flow of each of the pumps. The sensors 631 and 651 to activate the opening of the clamps are permanently fixed at any point beyond the $\theta_1$ angle of the rotating arms, but way before the cam starts to close the clamp. The sensors 632 and 652 that activate the closure of their respective clamps are normally set and locked at a point slightly before the cam closes the clamps. When the closing sensor 632, 652 is moved clockwise beyond the point where the cam normally closes the clamp, the stationary occluder remains far away from the push rod 636 and therefore the clamp continues to be open until the reflecting plate 630 has rotated enough to meet the sensor 652, 632 at the newly chosen angle at which point the solenoid is activated moving back its respective occluders of the clamp to occlude the tube against the push rod 636. This delayed closure of the tube outlet clamp creates the desired transient back flow. By adding a mechanical locking mechanism to the solenoid driven portion of the clamp itself, i.e., the occluder can be kept in the closed position, and truly stationary, as it would normally be used, mechanically, without the need of activating the solenoid when the back flow is not desired.

Each of the pumps (upper deck pump with the larger stroke volume, and the lower deck pump with the smaller stroke volume) will function separately exactly as the desired pulsatile monoroller pump. Since they are superimposed and share the same rotational axis, the flow rate of one pump can not be changed, by adjusting speed of rotation or pulse frequency, without influencing that of the other pump. Since in the great majority of patients needing biventricular support (right and left ventricles or hearts), the right heart requires less assist flow rate to begin with and recovers sooner than the left, the need for different assist flow rates becomes obvious. This pump is designed so that the lower deck pump has a smaller stroke volume, and therefore lower flow rate than the upper deck pump. In addition, the lower deck raceway is modular, so that the effective arc length can be made shorter, decreasing further the stroke volume. If a change of the stroke volume is not desired but the net forward flow needs to be decreased, then a transient period of back-flow can be created by making the outlet tube clamp close after the roller has left the raceway. Adjusting the amount of back-flow by controlling the timing of the outlet clamp closure in relation to the cycle of the pump, will effectively curtail the net forward flow of one pump while keeping the same r.p.m. to maintain the upper deck pump flow rate constant. When the time comes that the left heart assist pump flow rate needs to be decreased, but maintaining the same stroke volume and frequency (r.p.m.) are desirable, the closure time of the outlet clamp can similarly be moved to allow some back-flow, thus decreasing the net forward minute flow rate. Delivering a full stroke volume at a relatively fast frequency or r.p.m., maintains an effective washout phenomenon, an important factor to avoid clotting inside the tubing, which is apt to occur at low r.p.m. or pulse frequency. This problem mars even the specially designed cardiac assist valved pumps (pneumatically driven sac types, or electrically driven pusher plate types) when used at low flow rate. The capabilities of maintaining an effective wash out by the high flow velocity created by the transient regurgitation and the subsequent back and forth flow, should be an important adjunct of this type of assist pump, and useful during the weaning period of the patient, at which time pump flow reduction must be induced. The economic implications of this pump are great in this age of high medical costs, since this system does not require expensive cardiac valve prosthesis in order to generate pulsatile flow that all currently available assist devices must use. Although designed for extended cardiac assist, this biventricular assist dual monoroller pulsatile pump can also be used as a pulsatile pump during ordinary cardiac surgical procedures.

What is claimed is:

1. A pulsatile flow delivery apparatus, comprising:
   (a) a horse shoe shaped raceway having an inner side of a prescribed curvature;
   (b) a tube for flowing a fluid therethrough, said tube having a pump head portion disposed along the inner side of said raceway;
   (c) milking means comprising a pivot shaft, a rotating arm fixedly secured to said shaft and a single milking roller rotatably mounted on one end of said rotating arm, said milking means being disposed so that, as said rotating arm rotates, said milking roller travels along the inner side of said raceway to squeeze said pump head portion of said tube against said raceway, to thereby milk the pump head portion intermittently as said rotating arm rotates;
   (d) occlusive clamp means for opening and closing a portion of said tube downstream said pump head portion, said clamp means including a stationary component, a mobile component disposed in opposed relation to said stationary component, and an actuator connected to said mobile component for moving said mobile component toward and away from said stationary component to clamp and release said downstream portion of said tube; and
   (e) control means connected to said actuator of said clamp means for controlling timing for opening and closing said clamp means to thereby cause said fluid to flow from said tube in a pulsatile fashion, said control means comprising inlet sensing means for producing an inlet signal to open said clamp means after said roller travels a predetermined curvature angle along said raceway, and outlet sensing means for producing an outlet signal to close said clamp means just before said roller leaves said raceway.

2. A pulsatile flow delivery apparatus according to claim 1, in which said tube is made of a material with a rubber hardness code of between SHORE (A) 45.92 and SHORE (A) 55.93.

3. A pulsatile flow delivery apparatus according to claim 2, in which the curvature of said raceway is defined by an arc of 180° to 190°.

4. A pulsatile flow delivery apparatus according to claim 2, further comprising a second horse shoe shaped raceway having an inner side of a smaller curvature than the first-mentioned raceway; a second tube for flowing the fluid therethrough, said second tube having a pump head portion disposed along the inner side of said second raceway, said second tube being made of said material; and second milking means comprising a second rotating arm fixedly secured to said pivot shaft, at least two second rollers rotatably mounted on one end of said second rotating arm, said second milking means being disposed so that, as said second rotating arm rotates, said second roller travels along the inner side of said second raceway to squeeze said pump head portion of said second tube against said second raceway to thereby milk the pump head portion of the second tube intermittently.

5. A pulsatile flow delivery apparatus according to claim 2, and further comprising a second horse shoe shaped raceway having an inner side of a curvature different from that of the first-mentioned raceway; a second tube for flowing the fluid therethrough, said second tube having a pump head portion disposed along the inner side of said second raceway, said second tube being made of said material; second milking means comprising a second rotating arm fixedly secured to said pivot shaft, a single second roller rotatably mounted on one end of said second rotating arm, said second milking means being disposed so that, as said second rotating arm rotates, said second roller travels along the inner side of said second raceway to squeeze said pump head portion of said second tube against said second raceway to thereby milk the pump head portion of the second tube intermittently; second clamp means for opening and closing a portion of said second tube downstream said pump head portion thereof; and second control means being connected to said second clamp means for controlling the timing for opening and closing said second clamp means, said second control means including second inlet sensing means for producing an inlet signal to open said second clamp means after said second roller travels a predetermined curvature angle along said raceway, and second outlet sensing means for producing an outlet signal to close said second clamp means just before said second roller leaves said second raceway.

6. A pulsatile flow delivery apparatus according to claim 4, in which the first-mentioned raceway and said second raceway are integrally formed with each other to provide a composite raceway having a tail end, said composite raceway being comprised of at least one stationary segment and at least one movable segment removably disposed at said tail end of said composite raceway.

7. A pulsatile flow delivery apparatus according to claim 5, in which the first-mentioned raceway and said second raceway are integrally formed with each other to provide a composite raceway having a tail end, said composite raceway being comprised of at least one stationary segment and at least one movable segment removably disposed at said tail end of said composite raceway.

8. A pulsatile flow delivery apparatus according to claim 3, in which said stationary component is comprised of a stationary nut member, a screw threaded into said stationary nut member and having a knob at one end thereof, and a fixing nut member threaded on said screw for fixing said screw in position.

9. A pulsatile flow delivery apparatus according to claim 9, in which said actuator is comprised of a solenoid.

* * * * *